United States Patent [19]

Burger et al.

[11] Patent Number: 5,759,556
[45] Date of Patent: Jun. 2, 1998

[54] SKIN CARE COMPOSITIONS CONTAINING CERTAIN CYCLIC ALIPHATIC UNSATURATED COMPOUNDS AND RETINOL OR RETINYL ESTER

[75] Inventors: Allan Robert Burger, Passaic; Koichi Iwata, Washington Township; Stewart Paton Granger, Paramus, all of N.J.; Anthony Vincent Rawlings, Warrington, England; Ian Richard Scott, Allendale, N.J.

[73] Assignee: Chesebrough-Pond's USA Co., Division of Conopco, Inc., Greenwich, Conn.

[21] Appl. No.: 722,538

[22] Filed: Sep. 27, 1996

[51] Int. Cl.$^6$ .......................................................... A61K 7/48
[52] U.S. Cl. .............................. 424/401; 424/59; 514/725; 514/844; 514/846; 514/937
[58] Field of Search .................. 424/401, 59, 725; 514/844, 846, 937

[56] References Cited

U.S. PATENT DOCUMENTS

| 4,722,939 | 2/1988 | Loev et al. ............................... 514/529 |
| 5,536,740 | 7/1996 | Granger et al. .......................... 514/392 |

*Primary Examiner*—Jyothsan Venkat
*Attorney, Agent, or Firm*—Rimma Mitelman

[57] ABSTRACT

Certain cyclic aliphatic unsaturated compounds which sufficiently inhibit LRAT or ARAT catalyzed esterification of retinol into inactive retinyl esters, have the same effect on keratinocytes as retinoic acid. Thus, effects of the retinol or retinyl esters in combination with these cyclic compounds are analogous to treatment with retinoic acid.

4 Claims, No Drawings

SKIN CARE COMPOSITIONS CONTAINING CERTAIN CYCLIC ALIPHATIC UNSATURATED COMPOUNDS AND RETINOL OR RETINYL ESTER

FIELD OF THE INVENTION

The present invention relates to skin care compositions containing certain cyclic aliphatic unsaturated compounds and retinal or retinyl ester.

BACKGROUND OF THE INVENTION

Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496–498; Ellis, C. N. et al., "Pharmacology of Retinols in Skin", Vasel, Karger, Vol. 3, (1989), pp.249–252; Lowe, N. J. et al., "Pharmacology of Retinols in Skin", Vol. 3, (1989), pp.240–248; PCT Patent Application No. WO 93/19743.

It is believed that the use of retinol or esters of retinol would be preferred over retinoic acid. Retinol is an endogenous compound which occurs naturally in the human body and is essential for normal epithelial cell differentiation. Retinol is also considered much safer than retinoic acid. Esters of retinol hydrolyze in-vivo to produce retinol. It is believed that retinal esters and retinol are metabolically converted in the skin into retinoic acid according to the following mechanism:

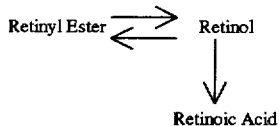

However, most of the endogenously applied retinol is rapidly converted into inactive fatty esters for storage in epidermal cells (keratinocytes). Esterification of retinol into inactive retinyl esters is achieved in cells by transfer of a fatty acyl group from an acyl CoA, catalyzed by the enzyme acyl CoA retinol transferase (ARAT), or by the transfer of an acyl group from phosphatidyl choline, catalyzed by the enzyme lecithin retinol acyl transferase (LRAT). These esterification reactions are very efficient in keratinocytes—the majority (95%) of cellular retinoids are in the form of retinyl fatty esters. Thus, unfortunately, although retinol and retinyl esters are safer to use than retinoic acid, they are less effective than retinoic acid at providing skin benefits.

The present invention is based, in part, on the discovery that certain cyclic hydrocarbons inhibit these esterification reactions and thus potentiate the action of retinol by increasing the amount of retinol available for conversion to retinoic acid. Thus, a mixture of selected cyclic hydrocarbons with retinol or retinyl esters mimics retinoic acid yet is safer to use than retinoic acid.

SUMMARY OF THE INVENTION

The present invention includes, in part, a skin conditioning composition containing:

(a) from about 0.001% to about 10% of retinol or a retinyl ester;

(b) from about 0.0001% to about 50% of a cyclic aliphatic unsaturated compound which at 100 µM concentration inhibits at least 20% of LRAT or ARAT catalyzed retinol esterification as measured by an in vitro Microsomal Assay; and (c) a cosmetically acceptable vehicle.

The cyclic aliphatic unsaturated hydrocarbons suitable for use in the present invention are aliphatic unsaturated aldehydes, ketones alcohols and esters.

The term "conditioning" as used herein means prevention and treatment of dry skin, photodamaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation.

The presence of the selected cyclic hydrocarbon in the inventive product substantially improves the performance of retinol or a retinyl ester.

According to the present invention, by virtue of including an effective amount of a selected cyclic aliphatic unsaturated compound which at 100 µM concentration inhibits at least 20% of LRAT catalyzed retinol esterification as measured by in vitro Microsomal Assay, into compositions containing retinol or a retinyl ester, the performance of the compositions is substantially improved.

DESCRIPTION OF THE PREFERRED EMBODIMENT

The inventive compositions contain, as a first essential ingredient, a compound selected from the group consisting of retinol or a retinyl ester. The term "retinol" includes the following isomers of retinol: all-trans-retinol, 13-cis-retinol, 11-cis-retinol, 9-cis-retinol, 3,4-didehydro-retinol. Preferred isomers are all-transretinol, 13-cis-retinol, 3,4-didehydroretinol, 9-cis-retinol. Most preferred is all-transretinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_6$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest. Retinyl linoleate is also preferred due to its efficacy.

Retinol or retinyl ester is employed in the inventive composition in an amount of from about 0.001% to about 10%, preferably in an amount of from about 0.01% to about 1%, most preferably in an amount of from about 0.01% to about 0.5%.

The second essential ingredient of the inventive compositions is a selected cyclic aliphatic unsaturated compound.

The cyclic aliphatic unsaturated compound suitable for use in the present invention inhibits at 100 μM concentration, at least 20% of LRAT or ARAT catalyzed retinol esterification as measured by in vitro Microsomal Assay. The in vitro Microsomal Assay employed for determining the suitability of the inclusion of the compound in the inventive compositions is as follows:

In vitro Microsomal Assay:

Microsomes are obtained as described in: J. C. Saari and D. L. Bredberg, "CoA and Non-CoA Dependent Retinol Esterification in Retinal Figment Epithelium" J. Biol. Chem. 263, 8084–90 (1988).

A solution containing 0.1M sodium phosphate pH 7 buffer, 5 mM dithiothreitol, 2 mg/ml bovine serum albumin, 40 micromolar palmitoyl CoA, 40 micromolar dilauroyl phosphatidyl choline, 10 micromolar retinol and a test compound or a solvent blank, is incubated for 1 hour at 37° C. with a microsomal fraction isolated from bovine retinal pigment epithelial cells. After incubation, the reaction was quenched by addition of an equal volume of ethanol, and the retinyl esters formed (retinyl laurate from the LRAT catalyzed reaction and retinyl palmitate from ARAT catalyzed reaction) are extracted with hexane. The hexane layer is removed, evaporated under nitrogen, and the residue analyzed by HPLC on a 3.9×300 mm $C_{18}$ reversed phase column using a 80% methanol in tetrahydrofuran mobile phase and fluorescence detection (325 nm excitation, 480 nm emission) to quantitate the retinyl ester. The quantity of ester formed in the presence of the solvent blank is taken as 100%, and this is used to calculate the percent inhibition of ester formation for the compounds tested. As a control, an aliquot of microsomes is inactivated by boiling for 5 minutes, which results in at least 95% inhibition of ester formation.

In a preferred embodiment of the invention, a cyclic aliphatic unsaturated compound is selected which, at a 100 μM concentration, inhibits at least 40% of LRAT or ARAT catalyzed retinol esterification. A preferred cyclic aliphatic unsaturated compound is selected from cyclic aliphatic unsaturated aldehydes, ketones, alcohols and esters.

Suitable cyclic aliphatic unsaturated aldehydes, ketones, alcohols and esters include but are not limited to: alpha damascone, beta damascone, delta damascone, isodamascone, damascenone, alpha ionone, beta ionone, allyl alpha ionone, isobutyl ionone, alpha methyl ionone, gamma methyl ionone, brahmanol, sandanol, alpha terpineol, lyral, ethyl saffranate, and mixtures thereof. The structures of these compounds are as follows:

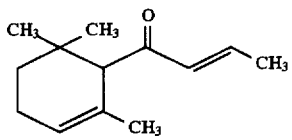

alpha-Damascone

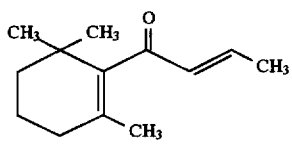

beta-Damascone

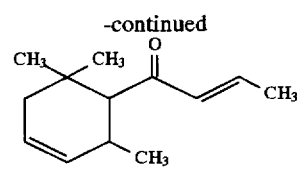

delta-Damascone

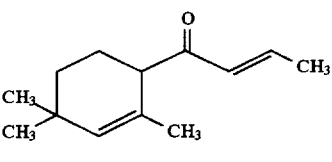

Isodamascone

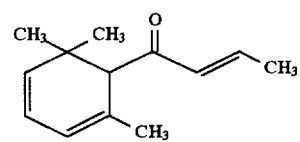

Damascenone

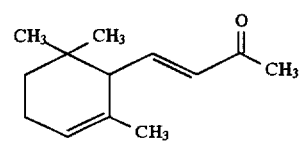

alpha-Ionone

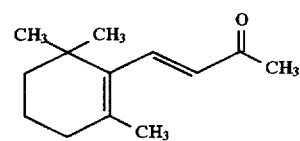

beta-Ionone

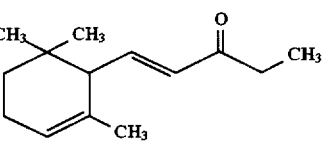

alpha-Methyl Ionone

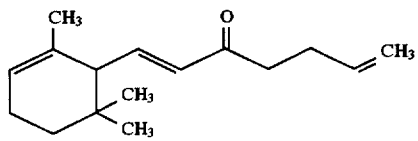

Allyl alpha-Ionone

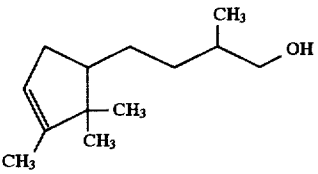

Brahmanol

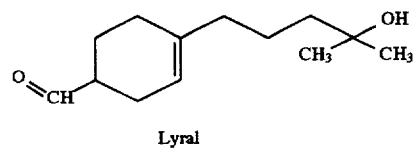

Lyral

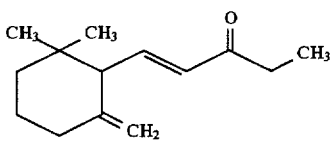

gamma-Methyl Ionone

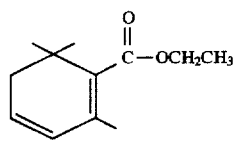

Ethyl Saffranate

Preferably, in order to maximize performance at a minimum cost, a cyclic aliphatic unsaturated compound is selected from the group consisting of damascones and ionones having the structures described above.

Most preferably, the cyclic aliphatic unsaturated compound is a α-Damascone and/or α-Ionone.

The cyclic aliphatic unsaturated compound is included in the inventive compositions in an amount ranging from about 0.0001% to about 50%, preferably from about 0.01% to about 10%, most preferably from about 0.1% to about 5%.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from about 5 to about 99.9%, preferably from about 25 to about 80% by weight of the composition, and can, in the absence of other cosmetic adjuncts, form the balance of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9,13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of cococaprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition. The cyclic compounds employed as actives in the present invention are, in addition to their role in the present invention, perfumes, and thus may have a dual function inventive compositions. Additional perfumes may be incorporated.

Use of the Composition

The composition according to the invention is intended primarily as a product for topical application to human skin, especially as an agent for conditioning and smoothening the skin, preventing or reducing the appearance of wrinkled or aged skin, skin lightening and sebum control.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion or a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

MATERIALS AND METHODS

Cell Culture

Human keratinocytes, isolated from neonatal foreskin by trypsin treatment were grown in Dulbecco Modification Eagle (DME) Hams F12 (1:1) medium/10% fetal calf serum in the presence of irradiated 3T3 mouse fibroblasts for establishing dividing keratinocyte colonies. Cells were grown under the above condition until their second passage and kept frozen for future use. Frozen second passage keratinocytes were thawed and plated into the above medium and grown for five days before they were switched to a serum-free MCDB 153-based medium keratinocyte growth medium (KGM) from Clonetics Corporation, San Diego, Calif., containing 0.15 mM Ca, or keratinocyte serum-free media (KSFM) from GIBCO containing 0.09 mM Ca). On day 7, when the cells were 80–90% confluent, they were trypsinized and plated in the serum-free medium for the various experiments.

Thymidine Assay $^3$H-Thymidine Incorporation and Keratinocyte Proliferation

The incorporation of $^3$H-thymidine by cultured keratinocytes was used as an assay of keratinocyte proliferation. Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$H-thymidine into a population of cells is proportional to the rate of DNA synthesis by this population of cells and therefore an indication of their cellular proliferation.

Keratinocytes (that were cultured as described above) were plated in 24 well plates at a density of about 20,000 cells per well in 1 ml media. After incubation for four days or until the cells were 60–70% confluent, the media was changed. Test compounds were added (in triplicate) to the wells 24 hours after the media change, and four hours later 1μCi $^3$H-Thymidine in 50 μl media was added per well. Cells were incubated for a further 24 hours. Media was removed from the cells, 10% ice cold trichloroacetic acid (TCA) added and plates were incubated on ice for 30 minutes. Cells were washed five times with 5% TCA and allowed to dissolve in 500 μl 0.1M NaOH for at least one hour (usually overnight). The preparations were neutralized with 0.1M HCl; 50 μl of the cell preparation was used to determine total protein content. Disintegrations per minute (DPM) from $^3$H labelling of DNA was determined by liquid scintillation counting of 900 μl of the cell preparation. Thymidine incorporation results were expressed as DPM/μg protein.

TRANSGLUTAMINASE ASSAY

Transglutaminase Assay and Keratinocyte Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of N $^ε$-(γ-glutamyl) lysine isodipeptide bonds catalyzed by the action of at least two different transglutaminases (TGases) expressed in the epidermis. TGase I is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

For Example 1, the following procedure was used:

Keratinocytes (cultured as described above) were plated in 96 well plates at a density of 3,000 cells per well in 200 μl media. After incubation for four days the media was changed to media containing test compounds (six replicates per test). The cells were cultured for a further 72 hours after which time the media was aspirated and the plates stored at −70° C. Plates were removed from the freezer, and the cells washed with PBS. 100 µl sterile water was added and the cells were freeze fractured by freezing at −70° C. then thawing. The cells were incubated for one hour at room temperature (R/T) with PBS/3% BSA (wash buffer, bovine serum albumin), then rinsed with a fresh aliquot of wash buffer. Cells were incubated with 50 µl of primary antibodies monoclonal anti-human transglutaminase mouse antibody (IgG) obtained from Biomedical Industries diluted 1:2,000 in wash buffer for one hour, 37° C. then rinsed two times with wash buffer. Cells were then incubated with 50 µl of secondary antibody (Fab fragment, peroxidase conjugated anti-mouse IgG obtaining from Amersham) diluted 1:4,000 in wash buffer for one hour at 37° C., then rinsed two times with wash buffer. Cells were incubated with substrate solution (4 mg o-phenylene diamine and 3.3 µl 30% $H_2O_2$ in 10 ml 0.1M citrate buffer pH 5.0) for five minutes, R/T, in darkness (under aluminum foil). The reaction was stopped by the addition of 50 µl 4N $H_2SO_4$. The absorbance of samples was read at 492 nm in the plate reader. Out of the six replicates, four were treated with both antibodies, two were treated only with the secondary antibody (i.e., to determine background binding of enzyme conjugated Ab). TGase levels were determined by subtracting background from the readings from each treatment and determining mean±s.d. for the replicates exposed to both Ab.

For Example 4, the following procedure was used:

Keratinocytes (cultured as described above) were plated in 96 well plates at a density of 3,000 cells per well in 200 µl of cell culture media. After incubation for four days, the media was changed to media containing test compounds (six replicates per test). The cells were cultured for a further 72 hours after which time the media was aspirated and the plates stored at −70° C. After the plates were removed from the freezer, the cells were further freezed fractured by freezing and thawing and then washed 3× with PBS. The cells were incubated for one hour at room temperature (R/T) with TBS/5% BSA buffer. Cells were then incubated with 100 µl of monoclonal anti-human transglutaminase (IgG) mouse antibody (primary antibody) obtained from Biomedical Technologies Inc. diluted 1:2000 in TBS/1% BSA buffer for two hours at 37° C., and then rinsed six times with wash buffer (TBS/1% BSA/0.05% Tween-20). Cells were next incubated with 100 µl of Fab fragment, peroxidase conjugated anti-mouse IgG antibody (secondary antibody) from Amersham diluted 1:4,000 in wash buffer for two hours at 37° C. and then rinsed three times with wash buffer and three times with PBS. Cells were incubated with substrate solution (4 mg o-phenylene diamine and 3.3 µl 30% $H_2O_2$ in 10 mL 0.1M citrate buffer, pH 5.0) for five minutes at R/T and in darkness (under aluminum foil). The reaction was stopped by the addition of 50 µl 4N H2SO4. The absorbance of samples was read at 492 nm in the plate reader. Out of the six replicates, four were treated with both antibodies, two were treated only with the secondary antibody (i.e., to determine the background binding of the enzyme conjugated antibody). Transglutaminase I levels were determined by subtracted background from the readings from each treatment and determining the mean s.d. for the replicates exposed to both antibodies.

DNA Assay

The level of TGase-1 detected after treatment of the cells could be influenced by cell number, i.e., the greater the number of cells the greater the level of TGase-1 detected. The level of TGase-1 was normalized to DNA content of the cells in the same well thus eliminating variation due to differences in cell number. DNA quantitation is a particularly useful indicator of cell number, including keratinocyte cell number, because each cell has to all intents and purposes an identical genome and therefore an identical quantity of DNA. The total DNA content of a well of cells therefore is directly proportional to the cell number in that well. Quantitation of DNA was used to normalize the TGase data to cell number.

Keratinocytes were plated in 96 well plates at a density of 3,000 cells per well in 200 µl media. After incubation for four days the media was changed for media containing test compounds (6 replicates per test). The cells were cultured for a further 72 hours after which time the media was aspirated and the plates stored for at least 1.5 hours at −70° C. Plates were removed from the freezer and thawed for 30 minutes. 100 µl/well of Hoechst dye (1 µg/ml final concentration) was added and this was incubated for 15 minutes, covered and then read in a fluorimeter (ex. 360 nm and em. 460 nm). The dye solution was removed and the wells were rinsed with PBS in preparation for the TGase assay.

EXAMPLE 1

Retinoic acid is more effective than retinol at altering keratinocyte differentiation state A. The effect on incorporation of $^3$H-thymidine µg soluble protein 24 hours after the addition of retinoic acid or retinol at various concentrations was examined. The results that were obtained are summarized in Table 1A.

TABLE 1A

Effect of Retinoic Acid (RA) and Retinol (ROH) on Keratinocyte Thymidine Incorporation

| Treatment | mean Thymidine incorp./µg protein ± s.d (% control) | p value vs Control | p value vs $10^{-7}$ M ROH | p value vs $10^{-8}$ M ROH | p value vs $10^{-9}$ M ROH |
|---|---|---|---|---|---|
| Control | 2094 ± 140 (100%) | — | 0.202 | 0.501 | 0.203 |
| 2.5 × $10^{-7}$ M RA | 2475 ± 116 (118%) | 0.005 | 0.032 | 0.004 | 0.002 |
| 2.5 × $10^{-7}$ M ROH | 2218 ± 73 (106%) | 0.202 | — | 0.021 | 0.005 |
| 2.5 × $10^{-8}$ M RA | 2686 ± 72 (128%) | 0.001 | 0.001 | 0.001 | 0.001 |
| 2.5 × $10^{-8}$ M ROH | 2034 ± 46 (97%) | 0.501 | 0.021 | — | 0.121 |

TABLE 1A-continued

Effect of Retinoic Acid (RA) and
Retinol (ROH) on Keratinocyte Thymidine Incorporation

| Treatment | mean Thymidine incorp./μg protein ± s.d (% control) | p value vs Control | p value vs $10^{-7}$ M ROH | p value vs $10^{-8}$ M ROH | p value vs $10^{-9}$ M ROH |
|---|---|---|---|---|---|
| $2.5 \times 10^{-9}$ M RA | 2556 ± 80 (122%) | 0.001 | 0.006 | 0.001 | 0.001 |
| $2.5 \times 10^{-9}$ M ROH | 1977 ± 19 (94%) | 0.203 | 0.005 | 0.121 | — | n = 3

All concentrations of retinoic acid tested, i.e., $2.5 \times 10^{-7}$M, $2.5 \times 10^{-8}$ and $2.5 \times 10^{-9}$M, significantly increased keratinocyte proliferation over both the ethanol control and each of the $2.5 \times 10^{-7}$M, $2.5 \times 10^{-8}$M and $2.5 \times 10^{-9}$M retinol treatments and they did so in a dose dependant manner. This is consistent with retinoic acid having a greater stimulatory effect on epithelial proliferation than retinol.

B. The effect on Transglutaminase levels normalized to DNA content of the cells after addition of retinoic acid and retinol was examined and the results are shown in Table 1B.

TABLE 1B

| Treatment | mean TGase/ DNA × $10^{-4}$ ± s.d (% control) | p value vs Control | p value vs $10^{-7}$ ROH | p value vs $10^{-8}$ ROH | p value vs $10^{-9}$ ROH |
|---|---|---|---|---|---|
| Control | 2.44 ± 0.24 (100%) | — | 0.001 | 0.001 | 0.001 |
| $2.5 \times 10^{-7}$ M RA | 0.16 ± 0.11 (7%) | 0.001 | 0.001 | 0.001 | 0.001 |
| $2.5 \times 10^{-7}$ M ROH | 1.14 ± 0.22 (47%) | 0.001 | — | 0.001 | 0.001 |
| $2.5 \times 10^{-8}$ M RA | 1.34 ± 0.40 (55%) | 0.001 | 0.001 | 0.001 | 0.001 |
| $2.5 \times 10^{-8}$ M ROH | 1.89 ± 0.30 (77%) | 0.001 | 0.001 | — | 0.001 |
| $2.5 \times 10^{-9}$ M RA | 1.87 ± 0.49 (77%) | 0.001 | 0.001 | 0.784 | 0.001 |
| $2.5 \times 10^{-9}$ M ROH | 2.70 ± 0.59 (>100%) | 0.001 | 0.001 | 0.001 | — | n = 3

All concentrations of retinoic acid tested, i.e., $2.5 \times 10^{-7}$M, $2.5 \times 10^{-8}$M and $2.5 \times 10^{-9}$M decreased keratinocyte differentiation over both the ethanol control and did so to a significantly greater extent than each of the corresponding $2.5 \times 10^{-7}$M, $2.5 \times 10^{-8}$M and $2.5 \times 10^{-9}$M retinol treatments. The decrease in transglutaminase level was dose dependent for both retinoic acid and retinol. This is consistent with retinoic acid having a greater inhibitory effect on epithelial differentiation than retinol.

EXAMPLE 2

In vitro microsomal esterification of retinol:

Microsomes are obtained as described in: J. C. Saari and D. L. Bredberg, "CoA and Non-CoA Dependent Retinol Esterification in Retinal Pigment Epithelium" J. Biol. Chem. 23, 8084–90 (1988).

A solution containing 0.1M sodium phosphate pH 7 buffer, 5 mM dithiothreitol, 2 mg/ml bovine serum albumin, 40 micromolar palmitoyl CoA, 40 micromolar dilauroyl phosphatidyl choline, 10 micromolar retinol and a test compound or solvent blank, was incubated for 1 hour at 37° C. with a microsomal fraction isolated from bovine retinal pigment epithelial cells. After incubation, the reaction was quenched by addition of an equal volume of ethanol, and the retinyl esters formed (retinyl palmitate from the ARAT catalyzed reaction, and retinyl laurate from the LRAT catalyzed reaction) were extracted with hexane. The hexane layer was removed, evaporated under nitrogen, and the residue analyzed by HPLC on a 3.9×300 mm C18 reversed phase column using a 80% methanol in tetrahydrofuran mobile phase and fluorescence detection (325 nm excitation, 480 nm emission) to quantitate the retinyl esters. The quantity of ester formed in the presence of the solvent blank was taken as 100%, and this was used to calculate the percent inhibition of ester formation for the compounds tested. As a control, an aliquot of microsomes was inactivated by boiling for 5 minutes, which resulted in at least 95% inhibition of ester formation.

The results that were obtained are summarized in Tables A and B.

The compounds in Table A were tested at a 100 μM concentration. The compounds in Table B were tested at a 10 μM concentration.

TABLE A

| COMPOUND | % INHIBITION, ARAT | % INHIBITION, LRAT |
|---|---|---|
| alpha damascone | 83 | 98 |
| beta damascone | 84 | 92 |
| delta damascone | 87 | 95 |
| isodamascone | 80 | 92 |
| damascenone | 70 | 79 |
| alpha ionone | 45 | 49 |
| beta ionone | 22 | 24 |
| allyl alpha ionone | 22 | 36 |
| isobutyl ionone | 8 | 45 |
| alpha methyl ionone | 67 | 77 |
| gamma methyl ionone | 21 | 38 |
| brahmanol | 70 | 75 |
| sandanol | 15 | 43 |
| alpha terpineol | 26 | 25 |
| timberol | 34 | 33 |
| lyral | 76 | 71 |
| tonalid | 50 | 33 |
| ethyl saffranate | 51 | 49 |
| traseolide | 41 | 21 |

TABLE B

| COMPOUND | % INHIBITION, ARAT | % INHIBITION, LRAT |
|---|---|---|
| alpha damascone | 67 | 87 |
| beta damascone | 45 | 52 |
| delta damascone | 58 | 64 |
| damascenone | 23 | 29 |
| allyl alpha ionone | 16 | 17 |

It can be seen from the results in Tables A and B that certain cyclic aliphatic unsaturated compounds are potent inhibitors of LRAT and ARAT catalyzed retinol esterification.

COMPARATIVE EXAMPLE 3

Example 2 was repeated with additional cyclic aliphatic unsaturated compounds. The results that were obtained are summarized in Table C.

The compounds in Table C were tested at a 100 μM concentration.

TABLE C

| COMPOUND | % INHIBITION, ARAT | % INHIBITION, LRAT |
|---|---|---|
| dihydro alpha ionone | 13 | 18 |
| alpha ionol | 0 | 0 |
| beta ionol | 0 | 0 |
| cinnamaldehyde | 0 | 0 |
| vanillin | 0 | 0 |
| eucalyptol | 0 | 0 |
| menthol | 0 | 0 |
| thymol | 0 | 0 |
| carvone | 0 | 0 |
| camphor | 0 | 0 |
| mentone | 0 | 0 |
| fenchyl alcohol | 12 | 4 |
| isocyclogeraniol | 18 | 16 |
| sandalone | 23 | 12 |
| dimethyl ionone | 0 | 9 |
| delta methyl ionone | 0 | 10 |

It can be seen from the results in Table C that not all cyclic aliphatic unsaturated compounds inhibit or sufficiently inhibit LRAT and ARAT catalyzed retinol esterification.

EXAMPLE 4

The effect on keratinocyte differentiation of compounds and combinations listed in Table D was examined. The results were expressed as % of control. Transglutaminase level was normalized to DNA. Data are from two experiments where the retinol concentration was changed. The results that were obtained are summarized in Table D.

TABLE D

| EXPERIMENT # | TREATMENT | CONCENTRATION mM | % CONTROL |
|---|---|---|---|
| 1 | Retinoic acid | .00025 | 24 |
| 1 | Retinol | .001 | 67 |
| 1 | α-Damascone | 1 | 92 |
| 1 | Retinol + α-Damascone | .001 + 1 | 34 |
| 2 | Retinoic acid | .00025 | 8 |
| 2 | Retinol | .00025 | 63.5 |
| 2 | α-Damascone | 1 | 86 |

TABLE D-continued

| EXPERIMENT # | TREATMENT | CONCENTRATION mM | % CONTROL |
|---|---|---|---|
| 2 | Retinol + α-Damascone | .00025 + 1 | 30 |

The results in Table D show that while α-Damascone alone and retinol alone were not very effective, the combination of the two attained synergistic reduction in transglutaminae mimicking the effect of retinoic acid on keratinocyte differentiation. This example also establishes a good correlation between microsomal assay and cell culture data.

EXAMPLE 5

This example illustrates a high internal phase water-in-oil emulsion incorporating the inventive composition.

| | % w/w |
|---|---|
| Retinol | 0.5 |
| Fully hydrogenated coconut oil | 3.9 |
| α-Damascone | 5 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 6

This example illustrates an oil-in-water cream incorporating the inventive composition.

| | % w/w |
|---|---|
| Retinol | 0.15 |
| Mineral oil | 4 |
| α-Ionone | 2 |
| Brij 56* | 4 |
| Alfol 16RD* | 4 |
| Triethanolamine | 0.75 |
| Butane-1,3-diol | 3 |
| Xanthan gum | 0.3 |
| Butylated hydroxy toluene | 0.01 |
| Water | to 100 |

*Brij 56 is cetyl alcohol POE (10)
Alfol 16RD is cetyl alcohol

EXAMPLE 7

This example illustrates an alcoholic lotion incorporating the composition according to the invention.

| | % w/w |
|---|---|
| Retinyl palmitate | 0.15 |
| α-methylionone | 0.5 |
| Ethanol | 40 |
| Butylated hydroxy toluene | 0.01 |
| Water | to 100 |

EXAMPLE 8

This example illustrates another alcoholic lotion containing the inventive composition.

|  | % w/w |
| --- | --- |
| Retinol | 0.15 |
| Lyral | 0.2 |
| Ethanol | 40 |
| Antioxidant | 0.1 |
| Water | to 100 |

EXAMPLE 9

This example illustrates a suncare cream incorporating the composition of the invention:

|  | % w/w |
| --- | --- |
| Retinol | 0.01 |
| Isodamascone | 0.3 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 10

This example illustrates a non-aqueous skin care composition incorporating the inventive combination.

|  | % w/w |
| --- | --- |
| Retinyl palmitate | 0.15 |
| α-Damascone | 1 |
| Silicone gum SE-30[1] | 10 |
| Silicone fluid 345[2] | 20 |
| Silicone fluid 344[3] | 55.79 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1]A dimethyl silicone polymer having a molecular weight of at least 50,000 and a viscosity of at least 10,000 centistokes at 25° C., available from GEC
[2]Dimethyl siloxane cyclic pentamer, available from Dow Corning Corp.
[3]Dimethyl siloxane tetramer, available from Dow Corning Corp.

Materials employed in the present invention are obtained from the following sources:

Palmitoyl CoA, BSA, dilauroylphospatidyl choline, retinol, retinoic acid dithiothreitol—from Sigma Cyclic aliphatic unsaturated compounds:

Damascones from Firmenich;

Ionones from IFF;

Others from suppliers listed in "Flavor and Fragrance Materials" 1991, by Allured Pub. Co.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin Care composition comprising:

(a) from about 0.001% to about 10% of retinol;

(b) from about 0.0001% to about 50% of a cyclic aliphatic unsaturated compound selected from the group consisting of alpha damascone, beta damascone, delta damascone, isodamascone, damascenone, alpha ionone, beta ionone, allyl alpha ionone, isobutyl ionone, alpha methyl ionone, gamma methyl ionone, brahmanol, sandanol, alpha terpineol, lyral, ethyl saffranate, and mixtures thereof; where in the cyclic aliphatic unsaturated compound at 100 μM concentration inhibits at least 20% of LRAT or ARAT catalyzed retinol esterification as measured by an in vitro microsomal assay, and (c) a cosmetically acceptable vehicle.

2. A skin care composition comprising:

(a) from about 0.001% to about 10% of retinol;

(b) from about 0.0001% to about 50% of a cyclic aliphatic unsaturated compound selected from the group consisting of alpha damascone, beta damascone, delta damascone, isodamascone, damascenone, alpha ionone, brahmanol, lyral, and mixtures thereof; where in the cyclic aliphatic compound inhibits at least 40% of LRAT or ARAT catalyzed retinol esterification and (c) a cosmetically acceptable vehicle.

3. The composition of claim 1 wherein the cyclic aliphatic unsaturated compound is selected from the group consisting of α-damascone, β-damascone, δ-damascone, isodamascone, damascenone, alpha Ionone, brahmanol, lyral, and mixtures thereof.

4. A method of treating a skin condition selected from the group consisting of dry skin, photodamaged skin, wrinkles, age spots, acne, skin lightening, psoriasis and atopic dermatosis, the method comprising applying to the skin the composition of claim 1.

* * * * *